United States Patent [19]
Teles et al.

[11] Patent Number: 5,585,496
[45] Date of Patent: Dec. 17, 1996

[54] CATALYTIC PREPARATION OF CONDENSATION PRODUCTS OF FORMALDEHYDE

[75] Inventors: Joaquim H. Teles, Ludwigshafen; Johann-Peter Melder, Mannheim; Eugen Gehrer, Ludwigshafen; Wolfgang Harder, Weinheim; Klaus Ebel; Carsten Groening, both of Ludwigshafen; Regina Meyer, Fussgoenheim, all of Germany

[73] Assignee: BASF Aktiengesellschaft, Ludwigshafen, Germany

[21] Appl. No.: 570,557

[22] Filed: Dec. 11, 1995

Related U.S. Application Data

[62] Division of Ser. No. 286,221, Aug. 5, 1994, Pat. No. 5,508,422, which is a division of Ser. No. 117,314, Sep. 7, 1993, Pat. No. 5,386,062.

[30] Foreign Application Priority Data

Sep. 11, 1992 [DE] Germany ............... 42 30 466.0

[51] Int. Cl.$^6$ ............... C07D 249/12; C07D 471/06
[52] U.S. Cl. ............... 548/264.2; 548/264.6; 546/64; 546/82
[58] Field of Search ............... 548/264.2, 264.6; 546/64, 82

[56] References Cited

U.S. PATENT DOCUMENTS 4,035,395  7/1977  Stetter et al. ............... 260/347.5

FOREIGN PATENT DOCUMENTS

| 054414 | 6/1982 | European Pat. Off. | ...... 548/264.2 |
| 246888 | 11/1987 | European Pat. Off. | ...... 548/264.2 |

OTHER PUBLICATIONS

Chemical Abstracts, vol. 104, No. 15, Apr. 1996, abstract no. 129501j.

*Primary Examiner*—Jacqueline Haley
*Attorney, Agent, or Firm*—Keil & Weinkauf

[57] ABSTRACT

A process for the catalytical preparation of condensation products of formaldehyde, in which formaldehyde or a formaldehyde-forming compound is caused to undergo reaction using a catalyst which has been produced, in the presence of an auxiliary base, from a triazolium salt of formula I

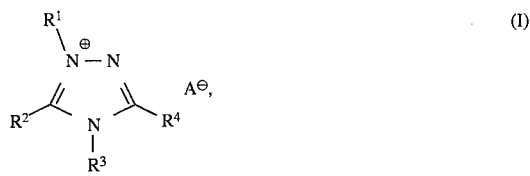

in which $R^1$ and $R^3$ are the same or different and stand for aliphatic groups having from 1 to 30 carbon atoms, optionally substituted aryl groups, optionally substituted aralkyl groups, and/or optionally substituted heteroaryl groups, $R^2$ represents hydrogen, the hydroxymethylene group —$CH_2OH$ or the hydroxy-hydroxymethylene-methylidyne group —$CH(OH)(CH_2OH)$, and $R^4$ denotes hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —$OR^5$, a thioether group —$SR^6$, an amino group —$NR^7R^8$, an acyl group—$COR^9$ or an ester group —$COOR^{10}$, where $R^5$, $R^6$, $R^7$, $R^8$, and $R^9$ stand for radicals such as those stated above for $R^1$, and $R^{10}$ is a $C_1$–$C_{10}$ alkyl group or an optionally substituted aryl or aralkyl group, or $R^3$ and $R^4$ together form a $C_3$–$C_5$ alkylene or $C_3$–$C_5$ alkenylene group or a $C_6$–$C_{14}$ alkylene group, or a $C_7$–$C_{14}$ aralkylene or $C_8$–$C_{14}$ aralkenylene bridging member, and A is the equivalent of an anion having one or more negative charges for electrical neutralization of the charge on the triazolium cation.

2 Claims, No Drawings

CATALYTIC PREPARATION OF CONDENSATION PRODUCTS OF FORMALDEHYDE

This is a divisional of application Ser. No. 08/286,221, filed Aug. 5, 1994, U.S. Pat. No. 5,508,422 which is a divisional of Ser. No. 08/117,314, filed Sep. 7, 1993 U.S. Pat. No. 5,386,062.

The present invention relates to a process for the catalytic preparation of condensation products of formaldehyde.

Following papers published by J. Castells (*Tetrahedron Letters*, 21, 4517 to 4520, (1980)) it is known in the art that thiazolium ylids can be used as catalysts for the catalytic pole reversal of formaldehyde and thus for its autocondensation to produce dihydroxyacetone and also for the corresponding conversion of higher aldehydes to acyloins.

Using thiazolium ylids as catalysts in the acyloin condensation of formaldehyde mainly ketones are obtained, in particular dihydroxyacetone (DHA). It is an object of the present invention to find a process, and novel catalysts, for the condensation of formaldehyde, which provide, in this reaction, a different spectrum of products from thiazolium ylids and which make possible, in particular, the preparation of the condensation products glycolaldehyde and/or glyceraldehyde in good selectivities. In particular, glycolaldehyde cannot be obtained with the aid of thiazolium ylid catalysts. Glycolaldehyde and glyceraldehyde are valuable intermediates for the preparation of ethylene glycol, glyoxal, glycerol and for the synthesis of active substances.

Accordingly, we have found a process for the catalytical preparation of condensation products of formaldehyde, wherein formaldehyde or a formaldehyde forming compound is caused to undergo reaction using a catalyst which has been produced, in the presence of an auxiliary base, from a triazolium salt of formula I

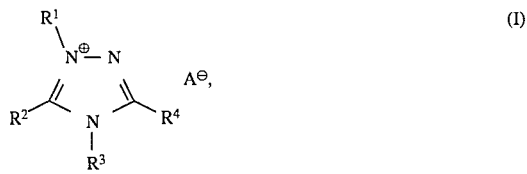

in which $R^1$ and $R^3$ are the same or different and stand for aliphatic groups having from 1 to 30 carbon atoms, optionally substituted aryl groups, optionally substituted aralkyl groups, and/or optionally substituted heteroaryl groups, $R^2$ represents hydrogen, the hydroxymethylene group —$CH_2OH$ or the hydroxy-hydroxymethylene-methylidyne group —$CH(OH)(CH_2OH)$, and $R^4$ denotes hydrogen, a nitro or cyano group, a halogen atom, an aliphatic group having from 1 to 30 carbon atoms, an optionally substituted aryl group, an optionally substituted aralkyl group, an optionally substituted heteroaryl group, an alkoxy group —$OR^5$, a thioether group —$SR^6$, an amino group —$NR^7R^8$, an acyl group $COR^9$ or an ester group —$COOR^{10}$, where $R^5$, $R^6$, $R^7$, $R^8$, and $R^9$ stand for radicals such as those stated above for $R^1$, and $R^{10}$ is a $C_1$–$C_{30}$ alkyl group or an optionally substituted aryl or aralkyl group, or $R^3$ and $R^4$ together form a $C_3$–$C_5$ alkylene or $C_3$–$C_5$ alkenylene group or a $C_6$–$C_{14}$ arylene group, or a $C_7$–$C_{14}$ aralkylene or $C_8$–$C_{14}$ aralkenylene bridging member, and A is the equivalent of an anion having one or more negative charges for electrical neutralization of the charge on the triazolium cation.

The catalysts to be used in the present invention are thus catalysts which are produced from 1,2,4-triazolium salts I in the presence of an auxiliary base. Since the radicals $R^1$, $R^3$ and $R^4$ usually only have an influence on the solubility properties of the triazolium salts and modify their reactivity and selectivity with reference to the formation of the different formaldehyde condensation products, these radicals can have a large number of meanings.

Thus $R^1$, $R^3$, and $R^4$ can be the same or different and stand for aliphatic groups having from 1 to 30 carbon atoms, such as $C_1$–$C_{30}$ alkyl and preferably $C_1$–$C_{10}$ alkyl groups, $C_2$–$C_{30}$ and preferably $C_2$–$C_{10}$ alkenyl or $C_2$–$C_{10}$ alkynyl groups having one or two, and preferably only one multiple bond, $C_3$–$C_{20}$ and preferably $C_3$–$C_{10}$ cycloalkyl or $C_3$–$C_{10}$ alkenyl-groups, $C_3$–$C_{20}$ heterocycloalkyl or $C_3$–$C_{20}$ alkenyl groups, such as piperidinyl, piperazinyl, pyrrolidinyl, imidazolidinyl, tetrahydrothienyl, tetrahydrofuranyl, tetrahydropyranyl, thiazolidinyl, oxazolidinyl, imidazolinyl, thiazolinyl, oxazolinyl or crown ether groups, $C_2$–$C_{30}$ and preferably $C_2$–$C_{10}$ alkoxy groups which are attached to the triazolium ring via a carbon atom and which have one or more, and preferably only one, oxygen atom in the ether chain, $C_1$–$C_{30}$ and preferably $C_1$–$C_{10}$ haloalkyl groups containing fluorine, chlorine and/or bromine and preferably fluorine and/or chlorine and more preferably fluorine, and having one or more, and preferably from one to three halogen atoms, whilst in the case of fluoroalkyl groups these may advantageously be perfluorinated fluoroalkyl groups, amino groups attached to the triazolium ring via a carbon atom, such as $C_2$–$C_{30}$ and preferably $C_2$–$C_{10}$ secondary amino groups, $C_3$–$C_{30}$ and preferably $C_3$–$C_{21}$ tertiary amino groups, optionally substituted aryl groups and preferably $C_6$–$C_{14}$ aryl groups, in particular phenyl, naphthyl, anthryl, or phenanthryl groups, optionally substituted $C_7$–$C_{20}$ aralkyl groups, in particular the benzyl, phenylethylene, or naphthylmethylene group, optionally substituted $C_2$–$C_{15}$ heteroaryl groups having one, two, or three nitrogen atoms or one oxygen or sulfur atom or having one or two nitrogen atoms and one oxygen or sulfur atom in the ring, such as the furanyl, thienyl, pyrrolyl, pyrazolyl, imidazolyl, oxazolyl, thiazolyl, isothiazolyl, isoxazolyl, pyridinyl, pyrimidinyl, pyrazinyl, chinolinyl, naphthyridinyl, 1,2,4-triazolyl or acridinyl groups.

Both the aliphatic and the aromatic and of course also the aralkyl radicals can be monosubstituted or polysubstituted, but preferably not more than trisubstituted, by halogen atoms or nitro, hydroxy, cyano, alkyl, alkoxy, or amino groups. Since these substituents usually exert only a slight effect on the catalytic activity of the catalysts produced from I or IV, it is preferred to use the aforementioned unsubstituted radicals $R^1$, $R^3$ and $R^4$, mainly due to the lower manufacturing costs involved.

In addition to having the above meanings, the radical $R^4$ can differ from the radicals $R^1$ and $R^3$ in that it may also be a hydrogen atom, a nitro or cyano group, a halogen atom selected from the group consisting of fluorine, chlorine, and bromine, an alkoxy group —$OR_5$ attached to the triazolium ring via the oxygen atom, a thioether group —$SR^6$ attached to the triazolium ring via the sulfur atom, an amino group —$NR^7R^8$ attached to the triazolium ring via the nitrogen atom, an acyl group —$COR^9$ or an ester group —$COOR^{10}$. The radicals $R^5$, $R^6$, $R^7$, $R^8$ and $R^9$ can have the same meanings as stated above for the radical $R^1$. Like the radicals $R^1$, the radicals $R^5$, $R^6$, $R^7$, $R^8$, $R^9$ and $R^{10}$ can also carry the substituents stated above for the radicals $R^1$, but it will usually be preferred, due to the lower manufacturing costs involved, to use unsubstituted radicals $R^5$, $R^6$, $R^7$, $R^8$, $R^9$, and $R^{10}$. Preferred radicals $R^5$, $R^6$, $R^7$, $R^8$, $R^9$, and $R^{10}$ are $C_1$–$C_{30}$ and especially $C_1$–$C_{10}$ alkyl groups, $C_6$–$C_{10}$ aryl groups, in particular the phenyl or naphthyl group and $C_7$–$C_{20}$ and preferably $C_7$–$C_{14}$ aralkyl groups, in particular the benzyl, phenylethylene, or naphthylmethylene group. A further preferred radical $R^7$ is the hydroxymethylene group.

In addition, the radical $R^4$ can form, together with the radical $R^3$, a $C_3$–$C_5$ alkylene or $C_3$–$C_5$ alkenylene bridging member a $C_6$–$C_{14}$ arylene bridging member and preferably an o-phenylene, o-naphthylene, 1,8-naphthylene, o-fluorenylene, 5,4-fluorenylene, o-phenanthrylene, 5,4-phenanthrylene, 9,10-phenanthrylene, o-anthrylene, 1,9-anthrylene, or a 2,2'-biphenylene bridging member, a $C_7$–$C_{14}$ aralkyl or $C_7$–$C_{14}$ aralkenylene bridging member, and these bridging radicals $R^3 \cap R^4$ can be monosubstituted, polysubstituted, but preferably not more than trisubstituted by halo, nitro, hydroxy, cyano, alkyl, alkoxy, or amino. Since these substituents usually exert only a slight effect on the catalytic activity of the respective catalysts produced from I, it is generally preferred to use unsubstituted bridging members $R^3 \cap R^4$, mainly on account of their lower-cost preparation. Since both the radical $R^3$ and the radical $R^4$ can contain the hetero-atoms nitrogen, oxygen or sulfur, the bridging member $R^3 \cap R^4$ can also contain these hetero-atoms, whilst it is preferred that said bridging member $R^3 \cap R^4$ contains not more than two, and in particular not more than one of said hetero-atoms.

The radical $R^2$, which is situated at what is presumed to be the catalytically active site of the triazolium compounds I, can represent hydrogen, the hydroxymethylene group —$CH_2OH$ or the hydroxy-hydroxymethylene-methylidyne group —$CH(OH)(CH_2OH)$.

The anions which form the anion-equivalent A for electrical neutralization of the charge on the triazolium cation may be of an arbitrary nature, theoretically, but preferably the non-nucleophilic anions of mineral acids or strong carboxylic acids are chosen. These anions can carry one or more, but preferably not more than three, negative charges. Negatively charged anions of this kind can electrically neutralize that number of triazolium cations which corresponds to the said number of negative charges, by which means the ions are held together by electrostatic forces, ie in the manner of a salt. The anion-equivalent A is thus equal to the molar amount of singly or multiply negatively charged anion required for the electrical neutralization of a molar amount of the triazolium cation, divided by its charge number.

Suitable anions are, for example, the anions of halides such as a fluoride, chloride, bromide, or iodide, or of a nitrate, tetrafluoroborate, tetraphenylborate, hexafluorophosphate, hexachloroplatinate, perchlorate, sulfate, phosphate, trifluoroacetate, methane sulfonate, or toluene sulfonate. Acid cation exchangers in their anionic form, for example, polyacrylates, sulfonated phenol-formaldehyde resins or sulfonated polystyrene can act equally well as polyanions. Preferably a halide, nitrate, tetrafluoroborate, or perchlorate is used as anion.

The mode of action of the triazolium salts I used in the invention is still largely unknown and it is only possible to put forward conjectures on the chemical mechanism underlying the process of the invention. The results of all prior experiments indicate, however, that the triazolium salt I is deprotonized by the auxiliary base in position 5 of the triazolium ring, to form the ylid-II which is mesomeric with the carbene-III (cf equation (1)),

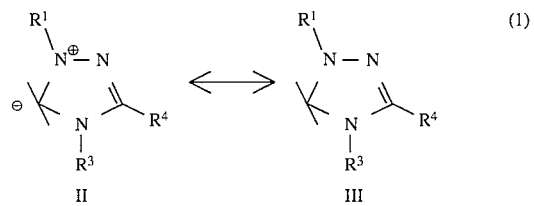

which is presumed to be the actual catalytically active species. Possibly, other catalytically active species of these triazolium compounds may be present under the conditions of the reaction, which may be derived from the ylid-II/carbene-III and form a state of equilibrium therewith. The condition required for the development of catalytic activity would appear, however, to comprise the formation of the reactive intermediate stage of the triazolium ylid/carbene-II/III, irrespective of the manner in which it occurs and of the starting materials which are used for the purpose. These considerations, however, merely serve as an attempt at an explanation of the reaction occurring in the present invention. If future research should reveal that other reactive intermediate stages than those postulated above catalyze the reaction of the invention, such findings should be regarded as having no significance with respect to the scope of protection of the present application, since said species are still produced by the measures of the invention.

The assumptions explained above are supported by the fact that in the reaction of the triazolium salts I with formaldehyde, addition compounds of triazolium salt/formaldehyde which are capable of being isolated in substance are formed, which are equivalent to the triazolium compounds I in which $R^2$=hydroxymethylene —$CH_2OH$ or hydroxy-hydroxymethylene-methylidyne —$CH(OH)(CH_2OH)$ and which, if they are caused to react separately with formaldehyde in the presence of an auxiliary base, are also catalytically active and catalyze the condensation of formaldehyde, in particular to form glycolaldehyde, glyceraldehyde, and tetroses.

Another factor pointing to the fact that position 5 of the triazolium ring is most probably the catalytically active site of these catalysts, is the fact that alcoholate or thiolate addition products of formula IV

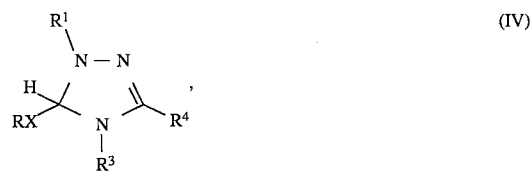

can be isolated in the reaction of alcoholates, for example, methanolates, or thiolates with the triazolium salts I, in which formula IV X stands for oxygen or sulfur, R is a $C_1$–$C_4$ alkyl group and preferably the methyl group, and $R^1$, $R^3$ and $R^4$ have the meanings stated above.

If these addition compounds IV, instead of the triazolium salts 1, are caused to react with formaldehyde under the reaction conditions usually employed in the process of the invention, but in the absence of the auxiliary base, formaldehyde condensation products are likewise formed, in particular glycolaldehyde, glyceraldehyde, and tetroses. Probably the alcohol or the thiol RXR is again eliminated from the compounds IV under the reaction conditions usually employed and what is presumedly the catalytically active ylid-II or carbene-III is produced, which can then develop its catalytic activity.

Furthermore, it is possible to heat the addition compounds IV alone, in solid form or in a high-boiling solvent, to cause elimination of the alcohol or thiol concerned and thus to produce compounds which are particularly active catalysts for the condensation of formaldehyde. Most probably the ylid-II or the carbene-III is formed in this thermolysis, or a compound acting similarly to these species.

Thus three types of embodiment apply to the process of the invention for the preparation of condensation products of formaldehyde:

α) The use of the triazolium salt compounds I as catalysts in the presence of an auxiliary base.

β) The use of the addition compounds IV as catalysts.

γ) The use of the thermolysis products obtained by the thermal elimination of the alcohols ROH or thiois RSH from the addition compounds IV, as catalysts.

Common to all three of the embodiments of the process of the invention is the fact that, according to the above explanations, the condensation of formaldehyde is catalyzed in effect by the same catalytically active species. All three of these embodiments are therefore mutually equivalent, although these three process embodiments are therefore mutually equivalent, although these three process variants have different advantages which govern the choice of embodiment to be used in any given case:

Variant α) has the advantage that it is not necessary to use further derivatives of the triazolium compounds I. The variants β) and γ) have the advantage that they can be carried out in the absence of an auxiliary base. Since the presence of an auxiliary base can possibly give cause for undesirable isomerization reactions and disproportionation reactions of formaldehyde condensation products in the reaction mixture, this advantage carries considerable weight when considering each individual case. The catalytically active compounds used as proposed in variant γ are particularly active catalysts. Particularly suitable for carrying out variant β) in the process of the invention are the methanolate-addition compounds IVa

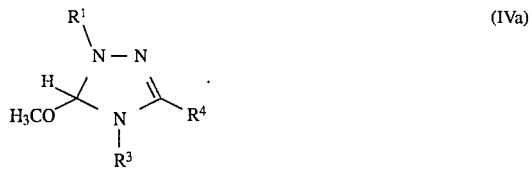

(IVa)

The process of the invention is advantageously carried out in the presence of a solvent. Examples of basically suitable solvents comprise a very wide range of solvents, such as alcohols, eg, methanol, ethanol, propanol, cyclohexanol, 2-ethylhexanol, and hexadecyl alcohol, amides, eg, dimethylformamide (DMF), dibutyl formamide, ureas, such as dimethylethylene urea, dimethylpropylene urea, carbonates, eg, propylene carbonate, ethylene carbonate, aromatic solvents, eg, toluene or xylene, heterocyclic compounds, eg, pyridine, N-methyl imidazol, N-methylpyrrolidone, ketones, eg, acetone, esters, eg, ethyl acetate, ethers, eg, methyl-tert-butyl ether, diethylene glycol dimethyl ether, dimethoxyethane, tetrahydrofuran, dioxane, nitro compounds, eg, nitrobenzene, nitrotoluene, nitromethane, tertiary amines, eg, triethylamine, halogenated hydrocarbons such as chloroform, dichloromethane, chlorobenzene, or dichlorobenzene, suifoxides, such as dimethyl sulfoxide, suifones, such as sulfolane, trioxan, and nitriles, eg, acetonitrile or propionitrile.

The amount of solvent used is not generally crucial and is dependent on the nature of the solvent employed, for which reason the amount of solvent giving the best results is advantageously determined empirically for each solvent. A number of bases can be used as auxiliary bases for activation of the triazolium salts I, which on account of their basicity are capable of deprotonizing the triazolium salts I in position 5 or the 5-hydroxymethylene or 5-[hydroxy(hydroxymethylene)methylidyne] derivates of the triazolium salts I. Nonnucleophilic bases are preferably used, for example, tertiary amines having from 3 to 30 carbon atoms or tertiary cyclic amines, and in particular cyclic amidines.

Suitable tertiary amines are, for example, trimethylamine, triethylamine, tripropylamine, tributylamine, ethyldiisopropylamine, decyldiethylamine, tridecylamine, quinuclidine, diazabicyclo-[2.2.2 ]-octane, N-methyl piperidine, N-ethyl piperidine, N-propyl piperidine, N-butyl piperidine, N,N'-dimethylpiperazine, N-methyl morpholine, dimethylbenzylamine, dibenzyimethylamine, benzyldioctylamine, benzyldiethylamine, cyclohexyldiethylamine, dicyclohexyldiethylamine, dicyclohexylmethylamine, dicyclohexylmethylamine, dicyclohexylethylamine etc. Triethylamine is most preferably used. Of the cyclic amidines the preferred compounds used are 1,5-diazabicyclo[4.3.0]non-5-ene, 1,8-diazabicyclo[5.4.0]undec-7-ene and 1,5,7-triazabicyclo[4.4.0]dec-7-ene.

Alternatively, polymeric tertiary amines can be used as auxiliary bases, for example, cross-linked styrene-divinylbenzene resins or phenol-formaldehyde resins which carry side chains containing tertiary amino groups or in which the aryl groups are substituted by dialkylamino groups. Such polymeric amines are usually used as anion exchangers.

Aromatic nitrogen bases can also be used, such as quinoline, pyridine or N-alkyl imidazoles, in particular N—(C₁-C₄ alkyl) imidazoles, for deprotonizing the triazolium salts I. Furthermore, inorganic bases, such as alkali metal and akaline-earth metal bicarbonates, such as alkali metal and akaline-earth metal carbonates or alkali metal carboxylates, in particular the sodium and potassium salts of $C_1$–$C_4$ carboxylic acids, can be used.

The use of polymeric tertiary amines in the form of anion exchangers makes it possible to prepare solutions of the ylids-II/carbens-III from the triazolium salts I which contain no auxiliary base. To achieve this end it is merely necessary to deprotonize the triazolium salts I over an anion exchanger resin carrying tertiary amino groups, for example, by passing a solution of the triazolium salt I over such an anion exchanger resin, and adding formaldehyde or a formaldehyde-forming compound to the solution of the resulting ylid-II/carbene-III only after this has passed through the anion exchanger. This technique has the advantage of largely suppressing the formation of by-products which could result from the Cannizzaro reaction of the condensation products formed.

In the process of the invention, the formaldehyde used can be in the form of formaldehyde or in the form of formaldehyde-liberating compounds, eg, as paraformaldehyde, formaldehyde hemiacetal solutions, gaseous formaldehyde or as an aqueous solution (Formalin®). It is generally stirred at temperatures ranging from 20° to 160° C. and preferably at from 50° to 120° C. and more preferably at from 60° to 80° C. advantageously for a period of from 5 to 500 min and preferably from 15 to 60 min together with the organic solvent and the catalyst. If the catalyst is produced in situ in the reaction mixture from the compounds of formula IV according to process variant β), temperatures of from 50° to 160° C. and preferably from 60° to 100° C. will generally be used. If, on the other hand, the catalytically active compounds produced in a separate thermolysis stage according to process variant γ) are used, the process can be carried out at a temperature ranging from 0° to 160° C. and preferably from 20° to 120° C.

The pressure applied is insignificant to the process of the invention, and it is therefore advantageous to operate under atmospheric pressure or under the autogenous pressure of the system.

The molar ratio of formaldehyde to catalyst can be, in all embodiments of the invention, in a range of from 10:1 to 30000:1. When using molar ratios of formaldehyde to catalyst of more than 200.1 a base or a buffer can be advantageously added to neutralize the acid.

As mentioned above, basically no auxiliary base is required for carrying out the process of the invention according to process variant β) or γ), since the catalysts are produced either in situ (variant β)) or ex situ (variant γ)) by elimination of RXH and preferably by the elimination of methanol, from the precursors IV. Since, however, acids can be formed to a slight extent during the reaction as a result of side reactions, for example, formic acid as a result of the Cannizzaro reaction of formaldehyde, and these acids can deactivate the catalyst, the addition of small amounts of base can be advantageous, for example a base such as is mentioned above as being suitable for use as an auxiliary base, in order to buffer or neutralize these acids. This may prove to be particularly advantageous when very small quantities of catalyst are used. It is thus possible, in such cases, to use an amount of base similar to that stated above with respect to variant α). However, it is advantageous to use smaller amounts of base. If the formaldehyde or formaldehyde-forming compound used is contaminated with acid, in particular formic acid, this is advantageously neutralized prior to use in the process of the invention for the reasons stated above, or the action of these acids in the process of the invention is compensated for in situ by the addition of an equivalent amount of base.

The reaction can be carried out either in a homogeneous phase or in suspension or even in a liquid two-phase system. In the latter case, aqueous formaldehyde may be used as starting material, for example, and the catalyst dissolved in an organic, water-immiscible solvent and preferably in a long-chain, in particular a $C_6$–$C_{20}$ alcohol. Under these phase transfer conditions the formaldehyde is extracted into the organic phase, where it reacts in contact with the catalyst, and the hydrophilic product (glycolaldehyde, glyceraldehyde) is then reextracted into the aqueous phase.

The triazolium salts I used in the process of the invention can be prepared by conventional methods, for example by the alkylation of mesoionic compounds, for example, the N-alkylation of nitron by means of alkyl halides or dialkysulfates (cf Busch et el: Bet.38, 4049 (1905)), by the oxidative desulfurization of the appropriately substituted triazoline-5-thiones (cf. Naturforsch. B, 25, 1421 (1970); J. Prakt. Chem., 330, 325 (1988)), which can in turn be obtained by the Lewis acid-catalyzed cyclization of the corresponding thiosemicarbazones, which can be prepared from the corresponding isothiocyanates following reaction thereof with an alkyl or aryl hydrazine to form the respective thiourea, and alkylation thereof with an aidehyde, (Bet. 42, 4596 (1909); Ber. 34, 320 (1901)). Triazolium salts I in which $R^4$ is an ether or thioether group which is attached to the triazolium ring via the hetero-atom are likewise synthesized starting from the corresponding isocyanates or isothiocyanates by reaction thereof with a hydrazine to produce the corresponding urea or thiourea derivative, and the formylation and cyclization thereof with formic acid and the subsequent alkylation of the resulting 1,2,4-triazoline-5-one or 1,2,4-triazoline-5-thione with an alkylizing agent (cf Ber. 42, 4596 (1909); J. Prakt. Chem. 67, 246 (1903); J. Prakt. Chem. 67, 263 (1903)).

Polycyclic triazolium salts I can be prepared from secondary methylamines following N-nitrosation thereof (Org. Synth., Coll. Vol. 2, 460 (1943)) and O-alkylation to form the corresponding alkoxydiazenium salt in a 1,3-dipolar cycloaddition with the respective N-heterocyclic compounds (cf Chem. Ber. 102, 3159 (1969)).

Triazolium salts I which carry a hydrogen atom in position 3 can be obtained, eg, by the process described in U.S. Pat. No. 4,388,761 by the reaction of 1,2,4-triazole with alkylizing or arylizing agents, such as alkyl halides or dialkylsulfates or aryl halides, in particular aryl fluorides. The 1,2,4-triazole is obtainable by the process described in Ainsworth et al, J. Am. Chem. Soc. 77, 621 (1955). Alternatively, 3(H)-triazolium salts I can be obtained by the process described in Boyd et al J. Chem. Soc. (C) 409 (1971) by the reaction of the corresponding oxadiazolium salts with a primary amine.

To effect production of the addition compounds IV the triazolium salt I concerned is generally caused to react in a solvent, for example, an ether such as tetrahydrofuran, dioxane, or dimethoxyethane or an alkanol, with the respective alkanolate or thiolate RXMe, in which Me is the gram-equivalent of a metal cation and preferably of an alkali metal cation, and x and R have the meanings stated above. Preferably, the alkanolates used are dissolved in the alcohol from which they have been formed. When carrying out the reaction of the alkanolates or thiolates RXMe with the triazolium salt I the process is generally carried out at a temperature ranging from 0° to 100° C. and preferably from 20° to 50° C. and a molar ratio of alcoholate or thiolate to triazolium salt I is used which is generally from 0.8:1 to 1.5:1 and preferably from 1:1 to 1.2:1. The addition product IV can be isolated by, say, filtration from the resulting reaction mixture following removal of the solvent used and separation of the resulting metal salts hardly soluble in organic solvents, and are used as such in the process of the invention.

For the purpose of producing the ylid/carbene II/III used in the process of the invention the addition compounds IV are heated in substance or in an inert, high-boiling solvent, eg, a paraffin or a sulfone, such as sulfolane (tetrahydrothiophene-1,1-dioxide), to temperatures of from 50° to 160° C. and preferably of from 60° to 140° C. and more preferably from 70° to 120° (2 until all of the alkanol or thiol RXH has separated from IV. The process can be carried out under the autogenous pressure of the system but it is preferred to operate under reduced pressure. The thermolysis product obtained in this thermolysis can be used directly as catalyst in the process of the invention.

EXAMPLES

Preparation of the catalysts

The triazolium salts I*a*, I*b*, I*c* and I*d* listed in the table below were prepared as disclosed in Eicher et al ((Chem. Ber. 102, 3159 (1969)).

The triazolium salt I*e* was prepared starting from N,N'-diphenylyl-N-aminothiourea (prepared as described in Ber. 42, 4596 (1909)):

To 20 g (82 mmol) of N,N'-diphenyl-N-aminothiourea there were added slowly and with external cooling 3.6 g (82 mmol) of freshly distilled acetaldehyde. The reaction mixture turned viscous before solidifying.

The resulting product was not subjected to further purification, but was taken up in 400 mL of ethanol and admixed, at 60° C., with a solution of 19.7 g (96 mmol) of iron(III) chloride in 5Oral of ethanol.

Following said addition, stirring was continued for a further hour at 60° C. and the ethanol then removed by vacuum distillation. The residue was dissolved in diethyl ether, and the ethereal phase was washed with water a number of times and dried over sodium sulfate. The solvent was distilled off, and the residue was recrystallized from petroleum spirit.

1,4-Diphenyl-3-methyl-1,2,4(5H)-triazoline-5-thione:

Mass spectrum:

molar peak 267 m/e melting point: 128° to 130° C.

conforming $^1$H- and $^{13}$C—NMR-spectra.

4.0 g (15 mmol) of 1,4-diphenyl-3-methyl-1,2,4(5H)-triazoline-5-thione were stirred with 60 mL of concentrated nitric acid, 60 mL water, and 14 mL of concentrated perchloric acid at room temperature. Following a reaction time of a few minutes solid material began to precipitate. On completion of the reaction, the solid was filtered off, washed successively with water, ethanol, and diethyl ether and dried in vacuo.

1,4-Diphenyl-3-methyl-1,2,4-triazolium perchlorate melting point: 218° C. (with decomposition)

conforming $^1$H- and $^{13}$C—NMR-spectra.

The triazolium salt If, characterised in the table below, was prepared by the prior method mentioned above in the descriptive portion of this application via the 2,3,4-triphenyl-substituted 1,2,4-triazoline-5-thione derivative.

1,3,4-Triphenyl-5-hydroxymethylene-1,2,4-triazolium perchlorate Ig:

5.0 g (12.5 mmol) of compound If, 4.0 g (133 mmol) of paraformaldehyde and 130 mL of tetrahydrofuran were heated at 80° C. for a period of 1 h in a glass autoclave. After cooling, the solvent was removed by vacuum distillation and the semi-solid residue was stirred with 10 wt % strength perchloric acid. The solidified residue was washed to neutrality with water and recrystallized from ethanol.

Melting point: 182° to 183° C.

conforming $^1$H- and $^{13}$C—NMR-spectra 2,4-Diphenyl-5-(N-methyl-N-phenylamino)-1,2,4-triazolium iodide Ih:

Nitron was prepared as disclosed in Ber. 38, 4049 (1905) and reacted with methyl iodide to form Ih according to the process cited in said reference.

2.0 g (4.4 mmol) of Ih were dissolved in 40.0 g of tetrahydrofuran at 55° C. under a blanket of argon together with 5.3 g (176 mmol) of paraformaldehyde and refluxed for a period of 5 h. The precipitated solid was filtered off while hot. The organic solution was diluted with 100 mL of dichloromethane, washed several times with water and dried over magnesium sulfate. Following separation of the solvent under reduced pressure there was obtained 1,4-diphenyl-5-hydroxymethylene-3-(N-methyl-N-phenylamino)-1,2,4-triazolium iodide Ii.

Melting point: 200° C.;

conforming $^1$H- and $^{13}$C—NMR-spectra 1,4-Diphenyl-3-(N-dodecy-N-phenylamino)-1,2,4-triazolium iodide Ij 2.0 g (6.4 mmol) of nitron and 9.5 g (32 mmol) of dodecyl iodide in 10 mL of toluene were heated at 100° C. for a period of 24 h under a blanket of argon. The precipitated crystalline product was filtered off from the cooled solution and recrystallized from ethanol/water.

Melting point: 129° to 130° C.;

conforming $^1$H- and $^{13}$C—NMR-spectra 1,4-Diphenyl-3-methoxy-1,2,4-triazolium tetrafluoroborate Ij 2.0 g (8.4 mmol) of 1,4-diphenyl-3-hydroxy-1,2,4-triazolium hydroxide interior salt (prepared as described in J. Prakt. Chem. 67, 263 (1903)) were suspended in 50 mL of dichloromethane. 1.3 g (9.2 mmol) of solid trimethyloxonium tetrafluoroborate were slowly added to this suspension at 0° C. The reaction mixture was stirred for a further 4 h at 0° C. The solid was then filtered off, washed with dichloromethane and recrystallized from ethanol. Ik was obtained in the form of a mixture, which consisted of 58 wt % of Ik, 23 wt % of starting compound and 19% of the isomeric 1,4-diphenyl-2-methyl-1,2,4-(3H)-triazolinium-3-one.

Compound II was prepared by the process described in J. Prakt. Chem. 67, 246 (1903).

1,3,4-Triphenyl-5-H-5-methoxy-1,2,4-triazoline IVa

To a solution of 7.0 g (25 mmol) of the compound If in 150 mL of methanol there were added, at room temperature, 1.4 g (26 mmol) of sodium methanolate, dissolved in 30 mL of methanol. The methanol was then removed under reduced pressure and the residue taken up in diethyl ether. The undissolved sodium perchlorate sediment was filtered off. The solid remaining following the removal of the solvent was recrystallized from methanol.

Melting point: 136° to 137° C.;

conforming $^1$H- and $^{13}$C—NMR-spectra

Ylid/carbene IIa/IIIa

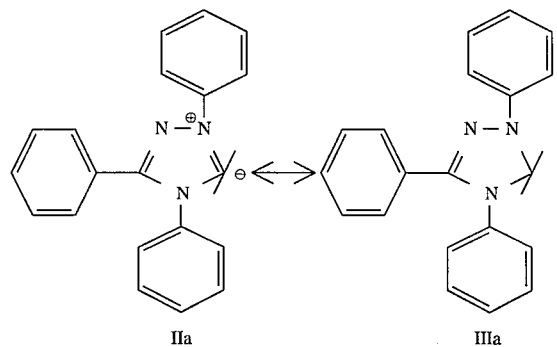

IIa  IIIa 1.0 g (3 mmol) of IVa was heated at 80° C. and under reduced pressure, until the loss of weight found was equal to that calculated for the elimination of the methanol. This was the case after a period of 16 h.

Standard test to determine the catalyst activity

The triazolium compounds Ia bis Ie described above were tested for catalytical activity as follows:

2.0 g (66 mmol) of paraformaldehyde were suspended in 18 g of DMF. To this suspension there were added 0.33 mmol of the triazolium compound concerned (molar ratio of formaldehyde to catalyst=200:1) and this batch was stirred for 30 min or for a period of 1 h at 80° C. The auxiliary bases used in the individual tests were each used in equimolar amounts with respect to the triazolium salt.

The reaction products were analyzed in the following manner: 0.5 g of reaction product was mixed with 10 g of oxidizing reagent (5.0 g of 1,4-butanediol as internal standard for gas chromatography and 70 g of hydroxylamine hydrochloride in 1000 g of pyridine), and heated at 70° C. for a period of 1 h. 1 mL of this solution was then mixed with 1 mL of hexamethyl disilazan and 1 mL trimethylsilyl chloride and left to stand for a period of from 0.5 to 1 h at room temperature until pyridinium chloride precipitated as large flakes. The mixture was filtered and the solution obtained used directly for the gas-chromatographic determination of the reaction products.

The results obtained with the different catalysts are listed in the following table. The abbreviations used in this table signify the following:

TABLE

| Catalyst | Time [min] | Temp. [°C.] | Base | Yield [%] | | | |
|---|---|---|---|---|---|---|---|
| | | | | GA | GlyAld | DHA | $C_4$ |
| 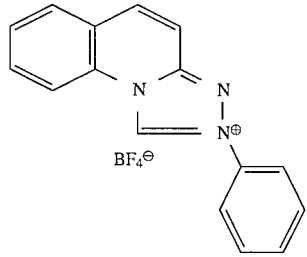<br>Ia | 30<br>60 | 80<br>80 | Et$_3$N<br>Et$_3$N | 2.9<br>4.1 | 0.3<br>0.9 | —<br>— | —<br>— |
| 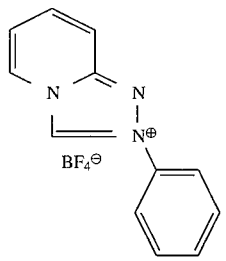<br>Ib | 30<br>60 | 80<br>80 | Et$_3$N<br>Et$_3$N | 18.2<br>27.7 | 3.4<br>10.9 | 0.2<br>0.6 | —<br>0.6 |
| 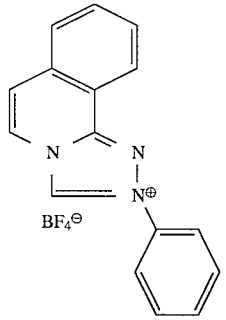<br>Ic | 30<br>60 | 80<br>80 | Et$_3$N<br>Et$_3$N | 21.3<br>40.6 | 3.0<br>13.1 | 0.3<br>0.5 | —<br>0.8 |
| 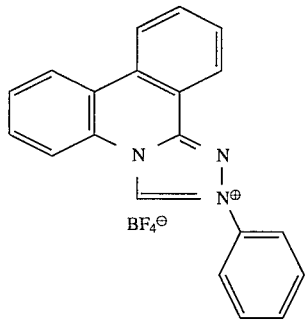<br>Id | 30<br>60 | 80<br>80 | Et$_3$N<br>Et$_3$N | 3.5<br>6.4 | 0.3<br>1.6 | 0.4<br>— | —<br>— |

TABLE-continued

| Catalyst | Time [min] | Temp. [°C.] | Base | Yield [%] | | | |
|---|---|---|---|---|---|---|---|
| | | | | GA | GlyAld | DHA | $C_4$ |
| Id | 60 | 80 | $Et_3N$ | 45.3 | 29.6 | 1.1 | 10.5 |
| If | 60 | 80 | $C_5H_5N$ | 9.2 | 0.2 | 0.2 | — |
| | 60 | 80 | $Et_3N$ | 41.2 | 33.4 | 1.3 | 26.5 |
| | 60 | 80 | NaOOCH | 27.0 | 21.0 | 3.3 | 28.0 |
| | 60 | 80 | NaOAc | 13.5 | 14.6 | 4.8 | 50.0 |
| Ig | 60 | 80 | $Et_3N$ | 20.7 | 34.8 | 2.4 | 28.7 |
| Ih | 60 | 80 | $Et_3N$ | 43.2 | 13.0 | 0.7 | 2.0 |

TABLE-continued
| Catalyst | Time [min] | Temp. [°C.] | Base | Yield [%] | | | |
|---|---|---|---|---|---|---|---|
| | | | | GA | GlyAld | DHA | $C_4$ |
| 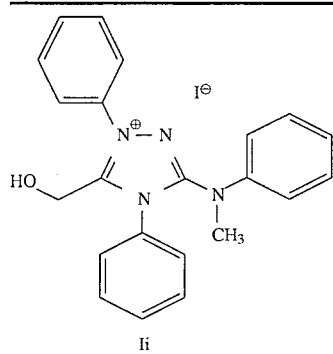 Ii | 60 | 80 | $Et_3N$ | 57.2 | 26.0 | 1.5 | 2.5 |
| 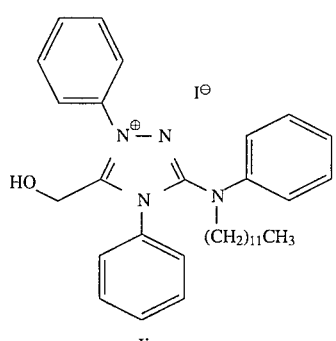 Ij | 60 | 80 | $Et_3N$ | 43.2 | 13.0 | 0.7 | 2.0 |
| 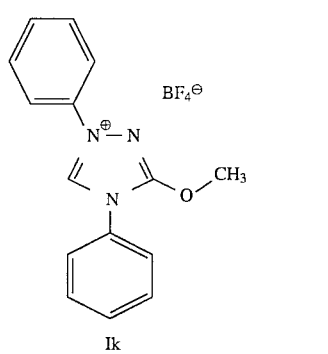 Ik | 60 | 80 | $Et_3N$ | 2.5 | 2.2 | 0.7 | — |
| 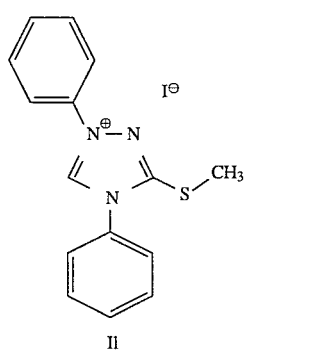 Il | 60 | 80 | $Et_3N$ | 19.7 | 19.7 | 8.6 | 7.3 |
GA glycolaldehyde
GlyAld glyceraldehyde
DHA dihydroxyacetone
$C_4$ mixture of $C_4$ carbohydrates (tetroses)
$Et_3N$ triethylamine
$C_5H_5N$ pyridine
NaOOCH sodium formate
NaOAc sodium acetate

Test on compound IVa for catalytic activity 15 mg (0.066 mmol) of IVa were stirred in 18 g of tetrahydrofuran with paraformaldehyde in a molar ratio of IVa to formaldehyde of 1:1000 at 80° C. for 15 min.

The resulting reaction products were subjected to gas-chromatographic analysis following the procedure described above.

| Yield: | |
|---|---|
| 62% | glycolaldehyde |
| 1% | glyceraldehyde |
| 11% | dihydroxyacetone |
| 1% | tetroses |

Catalyst activity test on the ylid/carbene IIa/IIIa obtained from compound IVa by thermal elimination of methanol 15mg of the ylid/carbene IIa/IIIa were stirred in 18 g of propionitrile at a temperature of 80° C. with paraformaldehyde in a molar ratio of catalyst to formaldehyde of 1:1500 for 45 min.

The resulting reaction products were subjected to gas-chromatographic analysis following the procedure described above.

| Yield: | |
|---|---|
| 60% | glycolaldehyde |
| 8% | glyceraldehyde |
| 3% | dihydroxyacetone |
| | no tetroses |

1-p-Nitrophenyl-4-methyl-1,2,4-triazolium iodide Im 5.00 (2.6 mmol) of 2-p-nitrophenyl-1,2,4-triazol, 4.1 g (29mmol) of methyl iodide and 20 mL of DMF were stirred in a glass autoclave for a period of 24 h at 100° C. Following the removal of the solvent, the residue was taken up in 100mL of dichloromethane, stirred for 30 min and the precipitated solid was filtered off.

Melting point: 213° to 216° C.

conforming $^1$H and $^{13}$C—NMR-spectra

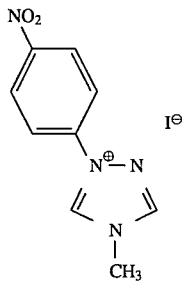

(Im)

2 g (66 mmol) of paraformaldehyde were suspended in 19 g of tetrahydrofuran. To this suspension there were added 0.33 mmol of Im and this batch was stirred for 120min at 80° C. The auxiliary base triethylamine was used in an amount equimolar to Im. The analysis of the products was carried out as stated above.

| Yield: | |
|---|---|
| 46.2% | glycolaldehyde |
| 0.7% | dihydroxyacetone |
| 4.1% | glyceraldehyde |

We claim:

1. A process for the preparation of addition compounds of triazolium salts of the formula IV

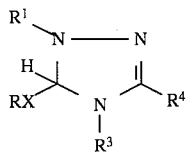

IV in which

X is oxygen or sulfur,

R is a $C_1$–$C_4$-alkyl, $R^1$ and $R^3$ are the same or different and stand for aliphatic groups having from 1 to 30 carbon atoms, optionally substituted aryl groups, optionally substituted aralkyl groups, and/or optionally substituted heteroaryl groups, $R^4$ denotes hydrogen, a halogen atom, a nitro or cyano group, an aliphatic group having from 1 to 30 carbon atoms, an optionally substituted aryl group, an optionally substituted aralkyl group, an optionally substituted heteroaryl group, an alkoxy group —$OR^5$, a thioether group —$SR^6$, an amino group —$NR^7R^8$, an acyl group —$COR^9$ or an ester group —$COOR^{10}$, where $R^5$, $R^6$, $R^7$, $R^8$ and $R^9$ stand for radicals such as those stated above for $R^1$, and $R^{10}$ is a $C_1$–$C_{30}$ alkyl group or an optionally substituted aryl or aralkyl group, or $R^3$ and $R^4$ together form a $C_3$–$C_5$ alkylene or $C_3$–$C_5$ alkenylene group or a $C_6$–$C_{14}$ arylene groups, and wherein the optionally substituted aryl, aralkyl and heteroaryl groups are substituted by a member selected from the group consisting of halogen, nitro, hydroxy, cyano, alkyl, alkoxy, and amino, and wherein a triazolium salt of the formula I

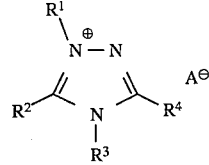

I in which $R^2$ is hydrogen, the hydroxymethylene group —$CH_2OH$ or the hydroxy-hydroxymethylene-methylidyne group —$CH(OH)(CH_2OH)$, and A is the equivalent of an anion having one or more negative charges for electrical neutralization of the charge on the triazolium cation and $R^1$, $R^3$ and $R^4$ have the above meanings, is caused to react with an alkanolate or thiolate of the formula RXMe in which R and X have the meanings given above and Me is the gram-equivalent of a metal-cation, at a temperature ranging from 0° C. to 100° C.

2. A process as defined in claim 1, wherein $R^1$, $R^3$ and $R^4$ are each phenyl and R is methyl.

* * * * *

UNITED STATES PATENT AND TRADEMARK OFFICE
CERTIFICATE OF CORRECTION

PATENT NO.: 5,585,496

DATED: December 17, 1996

INVENTOR(S): TELES et al.

It is certified that error appears in the above-identified patent and that said Letters Patent is hereby corrected as shown below:

On the cover page, item [57], in the Abstract, in formula I, delete the comma which appears after "A⊖".

On the cover page, item [57], in the Abstract, line 6 from the bottom, "$C_6$-$C_{14}$-alkylene" should be --$C_6$-$C_{14}$-arylene--.

Signed and Sealed this

Fourth Day of March, 1997

Attest:

BRUCE LEHMAN

Attesting Officer

Commissioner of Patents and Trademarks